US006900302B2

(12) United States Patent
Teti et al.

(10) Patent No.: US 6,900,302 B2
(45) Date of Patent: May 31, 2005

(54) VACCINE FORMULATIONS COMPRISING ANTIIDIOTYPIC ANTIBODIES WHICH IMMUNOLOGICALLY MIMIC GROUP B STREPTOCOCCAL CARBOHYDRATES

(75) Inventors: Giuseppe Teti, Messina (IT); Luciano Polonelli, Parma (IT)

(73) Assignee: Chiron S.r.l., Siena (IT)

( * ) Notice: Subject to any disclaimer, the term of this patent is extended or adjusted under 35 U.S.C. 154(b) by 0 days.

(21) Appl. No.: 10/703,886

(22) Filed: Nov. 7, 2003

(65) Prior Publication Data

US 2004/0101536 A1 May 27, 2004

Related U.S. Application Data

(62) Division of application No. 09/673,867, filed as application No. PCT/IB99/00799 on Apr. 20, 1999, now Pat. No. 6,676,938.

(30) Foreign Application Priority Data

Apr. 20, 1998 (GB) ............................................. 9808327

(51) Int. Cl.[7] ........................ C07H 21/02; C12N 15/00; C12N 5/06
(52) U.S. Cl. ................... 536/23.1; 435/320.1; 435/326; 435/327; 435/328; 435/329
(58) Field of Search ...................... 536/23.1; 435/320.1, 435/326, 328, 327, 329

(56) References Cited

U.S. PATENT DOCUMENTS

| | | |
|---|---|---|
| 5,476,784 A | 12/1995 | Rice et al. |
| 6,140,091 A | 10/2000 | Raso et al. |
| 6,444,787 B1 | 9/2002 | Pincus |

OTHER PUBLICATIONS

Ahlers et al., "construction of an HIV–1 peptide vaccine containing a multideterminant helper peptide linked to a V3 loop peptide 18 inducing strong neutralizing antibody responses in mice of multiple MHC haplotypes after two immunizations," Journal of Immunology 150:5647–5665, 1993.
Agadjanyan et al., "peptide mimicry of carbohydrate epitopes on human immunodeficiency virus," Nature Biotechnology 15:547–551, 1997.
Baker et al., "Role of antibody to native type III polysaccharide of group B streptococcus in infant infection," Pediatrics 68(4):544–549, 1981.
Baker et al., "Safety and immunogenicity of group B streptococcal (GBS) polysaccharide (PS) types Ia and Ib–tetanus toxoid (Ia–TT; Ib–TT) conjugate vaccines in women," Pediatric Research 39:abstract 980, 1996.
Baker et al., "Group B streptococcal infections," Remington J., Klein J.O., eds. Infectious Diseases of the Fetus and Newborn Infant, 4th ed., Chapter 26, 980–1054, 1995.

Baker et al., "Correlation of maternal antibody deficiency with susceptibility to neonatal group B Streptococcal infection," New England Journal of Medicine 294:753–756, 1976.
Bona, "idiotype vaccines: forgotten but not gone," Nature Medicine 4(6):668–669, 1998.
Clarkson et al., "In vitro selection from protein and peptide libraries," Trends in Biotechnology 12:173–184, 1994.
Cull et al., "Screening for receptor ligands using large libraries of peptide linked to the C terminus of the lac repressor," Proc. Natl. Acad. Sci. USA 89:1865–1869, 1992.
Cusumano et al., "Role of gamma interferon in a neonatal mouse model of group B Streptococcal disease," Infection and Immunity 64(8):2941–2944, 1996.
Feldman et al., "The group B streptococcal capsular carbohydrate: immune response and molecular mimiery," Advances in Experimental Medicine and biology, 435(435):261–269, 1998.
Griffiss et al., "Vaccines against encapsulated bacteria: a global agenda," Reviews of Infectious Diseases 9(1):176–181, 1987.
Hoogenboom, "Designing and optimizing library selection strategies for generating high–affinity antibodies," Trends in Biotechnology 15:62–70, 1997.
Kasper et al., "Immune response to type III group B streptococcal polysaccharide–tetanus toxoid conjugate vaccine," J. Clin. Invest. 98:2308–2314, 1996.
Kortt et al., "Recombinant anti–sialidase single–chain variable fragment antibody characterization, formation of dimmer and higher–molecular–mass multimers and the solution of the crystal structure of the single–chain variable fragment/sialidase complex," Eur. J. Biochem. 221:151–157, 1994.
Kumar et al., "Universal T Helper cell determinants enhance immunogenicity of a plasmodium falciparum merozoite surface antigen peptide," Journal of Immunology 148:1499–1505, 1992.
Larsson et al., "Experimental vaccination against group B Streptococcus, an encapsulated bacterium, with highly purified preparations of cell surface proteins rib and α," Infection and Immunity 64(9):3518–3523, 1996.
Lett et al., "Immunogenicity of polysaccharides conjugated to peptides containing T– and B–cell epitopes," Infection and Immunity 62(3):785–792, 1994.
Liao et al., "Isolation of a thermostable enzyme variant by cloning and selection in a thermophilc," Proc. Natl. Acad. Sci. USA 83:576–580, 1986thermophile.

(Continued)

Primary Examiner—S. Devi
(74) Attorney, Agent, or Firm—Roberta L. Robins; Rebecca M. Hale; Alisa A. Harbin (57) ABSTRACT

The invention relates to peptide, oligopeptide or polypeptide compounds that are capable of eliciting a protective immune response against the capsular polysaccharide of group *B Streptococcus* (GBS), particularly type III GBS. Such compounds are useful in the development of vaccines that are effective against diseases caused by these pathogens.

12 Claims, 2 Drawing Sheets

OTHER PUBLICATIONS

Madoff et al., "Protection of neonatal mice from group B streptococcal infection by maternal immunization with Beta C protein," Infection and Immunity, 60(12):4989–4994, 1992.

Magliani et al., "Therapeutic potential of antiidiotypic single chain antibodies with yeast killer toxin activity," *Nature Biotechnology* 15:155–158, 1997.

Magliani et al., "Neunatal mouse immunity against group B streotococcal infection by maternal vaccination with recombinant anti–idiotypes," *Nature Medicine* 4(6):705–709, 1998.

Mancuso et al., "Beneficial effects of interleukin–6 in neonatal mouse models group B streptococcal disease" *Infection and Immunity* 62(11):4997–5002, 1994.

Mancuso et al., "Role of interleukin 12 in experimental neonatal sepsis caused by group B streptococci," *Infection and Immunity* 65(9):3731–3735, 1997.

Mancuso et al., "Induction of tumor necrosis factor alpha by the group– and type– specific polysaccharides from type III group B Streptococci," *Infection and Immunity* 62(7):2748–2753, 1994.

Matteakis et al., "An in vitro polysome display system for identifying ligands from very large peptide libraries," *Proc. Natl. Acad. Sci. USA* 91:9022–9026, 1994.

McNamara et al., "Monoclonal idiotype vaccine against Streptococcus pneumonie infection," *Science* 226:1325–1326, 1984.

Panina–Bordignon et al., "Universally immunogenic T cell epitopes: promiscuous binding to human MHC class II and promiscuous recognition by T Cells," *Eur. J. Immunol.* 19:2237–2242, 1989.

Paoletti et al., "Neonatal mouse protection against infection with multiple group B Streptococcal (GBS) serotypes by maternal immunization with a tetravalent GBS polysaccharide–tetanus toxoid conjugate vaccine," *Infection and Immunity* 62(8):3236–3243, 1994.

Pincus et al., "Peptides that mimic the group B streptococcal type III capsular polysaccharide antigen," *Journal of Immunology*, 160(1):293–298, 1998.

Rubens et al., Transposon mutagenesis of type III group B Streptococcus: correlation of capsule expression with virulence.: *Proc. Natl. Acad. Sci. USA* 84:7208–7212, 1987.

Stein et al., "neonatal administration of idiotype or anti–idiotype primers for protection against *E. coli* K13 infection in mice," *J. Exp. Med.* 160:1001–1041, 1984.

Teti et al., "Synthesis and immunological properties of an O–stearoyl polysaccharide from group B Streptococci," *J. Immunol. Res.* 4:67–72, 1992.

Von Hunolstein et al., "Soluble antigens from group B Streptococci induce cytokine production in himan blood cultures," *Infection and Immunity* 65(10):4017–4021, 1997.

Westerink et al., "Development and characterization of an anti–idiotype antibody to the capsular polysaccharide of Neisseria meningitides serogroup C," *Infec. Immun.* 56:1120–1127, 1988.

Westerink et al., "Anti–idiotypic antibodies to bacterial capsular polysacchardies," *Idiotypic Network and Disease*, eds. Cerney & Hiernaux, Chapter 5 107–119, 1990.

Westerink et al., "Peptide mimicry of the meningococcal group C capsular polysaccharide," *Proc. Natl. Acad. Sci. USA* 92:4021–4025, 1995.

Winter et al., "Making antibodies by phage display technology," *Annu. Rev. Immunol.* 12:433–455, 1994.

Yelamos et al., "Targeting of non–Ig sequences in place of the V segment by somatic hypermutation," *Nature* 376:225–229, 1995.

VACCINE FORMULATIONS COMPRISING ANTIIDIOTYPIC ANTIBODIES WHICH IMMUNOLOGICALLY MIMIC GROUP B STREPTOCOCCAL CARBOHYDRATES

This application is divisional of U.S. Application Ser. No. 09/673,867, filed May 17, 2001, now U.S. Pat. No. 6,676,938, which is a §371 filing from PCT/IB99/00799, filed Apr. 20, 1999, which claims priority from GB 9808327.2, filed Apr. 20, 1998, from which applications priority is claimed pursuant to the provisions of 35 U.S.C. §§119/120 and which applications are incorporated herein by reference in their entireties.

The present invention relates to compounds that are capable of eliciting a protective immune response against the capsular polysaccharide of group B Streptococcus (GBS), particularly type III GBS. Such compounds are useful in the development of vaccines that are effective against diseases caused by these pathogens.

Group B streptococci (GBS) are recognised as a major cause of sepsis and meningitis in neonates and in susceptible adult patients such as those suffering from diabetes, cirrhosis and solid tumours. Although the use of antibiotics has had a dramatic impact on case fatality rate, the attack rates for infection have changed little. Indeed, even in industrialised countries, the incidence of mortality and permanent disability remains high in spite of appropriate therapy being applied.

GBS are classified into serotypes based on specific type of capsular polysaccharides (CHO) possessed by the organism. The capsular polysaccharide has anti-phagocytic properties and is considered to be the main virulence factor of GBS (Baker et al., 1995; Rubens et al., 1987). Capsular type III GBS are responsible for the majority of neonatal infection and for approximately 90% of meningitis cases (Baker et al., 1995).

Immunisation of fertile women with a combination of type-antigens has been proposed as a strategy for the prevention of neonatal disease, with the rationale that specific antibodies passing through the placental barrier can prevent neonatal infection (Baker et al., 1981). Indeed, a significant correlation has been shown between GBS infection in neonates and low levels of maternal antibodies to the type-specific CHO (Baker et al., 1981; Baker et al., 1976).

Polysaccharide vaccines have been developed in an attempt to control the incidence of diseases caused by GBS. The major problem with the capsular polysaccharide vaccines is their poor immunogenicity. This is believed to derive from the T-cell independent (TI) type of immune reaction that is the only antibody response used by the body against polysaccharide antigens. This type of response does not involve MHC Class II restriction molecules for antigen presentation to T-cells; as a consequence, T-cell help is prevented.

A widely accepted method to potentiate the immunogenicity of polysaccharide antigens is by their conjugation with proteins. To a large extent, this approach has been successful in the prevention of Haemophilus influenzae type b infections (Ala'Aldeen and Hormaeche, 1995). Type CHOs conjugated with tetanus toxoid (Paoletti et al., 1994; Kasper et al., 1996; Baker et al., 1996) or GBS proteins (Madoff et al., 1992; Larsonn et al., 1996) are currently being evaluated as potential vaccines for the prevention of GBS disease.

An alternative strategy to obtain effective and boostable antibody responses against carbohydrate antigens involves the development of protein molecules mimicking the conformation of relevant carbohydrate epitopes. The advantage of this approach is that, by their chemical nature, proteins have an intrinsic ability to stimulate T cell help in an antigen-specific way. This strategy resulted in the development of a monoclonal antiidiotypic antibody (mAb) coupled to a carrier protein that was successfully used as a surrogate vaccine to immunoprotect BALB/c mice against lethal Streptococcus pneumoniae infection (McNamara et al., 1984). Monoclonal antibodies mimicking the K13 Escherichia coli (Stein et al., 1984) and the group C Neisseria meningitidis (Westerink et al., 1988) capsular antigens have also been described.

However, although these reports illustrate the concept that compounds can be generated that to some extent mimic the antigenic determinants of capsular polysaccharides, it is widely-appreciated in the art that the specific compounds developed so far (mouse monoclonal antibodies) are unlikely human vaccine candidates and are often ineffective in conferring long-lasting protective immunity. Furthermore, no such compounds have to date been generated that are effective against GBS.

There thus remains a great need for the development of new, improved vaccine strategies that are effective in combating diseases caused by GBS and in particular for a compound that is capable of eliciting a protective immune response against GBS when used as a vaccine.

SUMMARY OF THE INVENTION

According to the present invention there is provided a peptide, oligopeptide or polypeptide compound that is capable of eliciting a protective immune response against the capsular polysaccharide of group B Streptococcus. Such compounds are useful as immunogenic compounds and may in turn be useful as components of vaccines that are protective against diseases caused by GBS.

Preferably, the compounds are capable of eliciting a protective immune response against the type III capsular polysaccharide of group B Streptococcus, which is widely recognised as being the major virulence determinant of GBS. Neonatal protection can be obtained by immunising mothers with these compounds.

By the term "protective immune response" is meant the development of a beneficial humoral response and/or a cellular response that is directed against the compound of the invention in an animal or human patient. A humoral response is antibody-mediated and involves the generation of antibodies with affinity for the compounds of the invention. This means that upon GBS invasion of an individual who has been immunised with a compound according to the invention, the individual's immune system will possess an immunologic memory of the compound and will be therefore able to mount an immediate humoral attack against the GBS organisms.

A cellular response is elicited by the presentation of antigenic epitopes in association with Class I or Class II molecules of the major histocompatibility complex (MHC). This activates antigen-specific CD4+ T helper cells or CD8+ cytotoxic T lymphocyte cells.

Species in which the compounds of the present invention may be effective in eliciting an immune response include all mammals, especially humans. In most cases, it will be preferred that the compounds are active eliciting an immune response in humans. The population of humans that are in greatest need of protection from disease caused by GBS are neonates. However, various sectors of the adult population are also at risk, particularly those who are suffering from debilitating chronic disease such as diabetes, cirrhosis or who carry a solid tumour.

An effective strategy to protect neonates involves the elicitation, in mothers, of antibodies that are capable of crossing the placental barrier. Such antibodies belong to the IgG class and are produced only in response to antigens capable of stimulating both B and T lymphocytes (T-dependent antigens). The compounds provided according to the present invention have the ability to stimulate the production of specific IgG. Moreover, maternal immunisation with these compounds is effective to protect neonates from GBS disease.

By peptide is meant a compound of between 3 and 10 amino acids covalently coupled together. An oligopeptide will comprise between 10 and 30 linked amino acids, whilst a polypeptide will contain greater than 30 amino acids.

The structure of the peptide, oligopeptide or polypeptide compounds according to the invention will be such as to contain in the folded three-dimensional structure an epitope that mimics an immunological determinant group of the capsular polysaccharide of group *B Streptococcus*. Preferably, this epitope mimics an immunological determinant group of the type III capsular polysaccharide of group *B Streptococcus*.

Peptides and oligopeptides are ideal candidates for use as immunogenic compounds due to their small size; these molecules are sufficiently large to mimic antigenic epitopes (that are typically determined by between 5 and 12 amino acids), yet are small enough to possess pharmacokinetic properties that are advantageous over those of more bulky molecules such as immunoglobulins. By their chemical nature, these molecules possess an intrinsic ability to stimulate T cell help in an antigen-specific fashion, a property not possessed, for example by polysaccharides. This is one reason why the use of polysaccharide vaccines suffers inherent drawbacks in the treatment of diseases caused by capsular pathogens.

Polypeptide compounds according to the invention may also possess advantageous properties that suit these compounds to certain applications. The properties of these molecules can be precisely tailored as desired, for example by grafting an Fc domain onto the molecule in order to allow recruitment of various effectors of the immune system.

According to a preferred embodiment of the present invention, a polypeptide compound effective in eliciting the desired immune response against the capsular polysaccharide of GBS may comprise an scFv fragment. These molecules are small and therefore possess advantageous pharmacokinetic properties. Their small sise also means that production of anti-scFv antibodies will be minimised. The generation of an anti-scFv response may also be minimised by constructing the scFv from molecules derived from the same species as the subject animal to be immunised. Most preferably, the compound of the present invention comprises the scFv C10, generated by selection of an scFv phage display library using the anti-type III CHO P9D8 mAb (Teti et al., 1992).

The peptides, oligopeptides or polypeptide compounds of the present invention may be fused to carrier proteins. A carrier protein is an antigenic polypeptide entity that induces the formation of antibodies directed against an antigen that is conjugated to it, by the immune system of an organism into which the carrier-antigen conjugate is introduced. The necessity to use carrier proteins derives from the fact that although many short epitopes are protective, they are often poorly immunogenic. This negates the usefulness of these epitopes in the generation of new and efficacious vaccines. By conjugating an immunogenic carrier protein to a molecule that is non-immunogenic, it is possible to confer the high immunogenicity of the carrier protein onto the conjugate molecule. Such conjugate molecules stimulate the generation of an immune response against the non-immunogenic portion of the conjugate molecule and thus have been used effectively in vaccines that protect against pathogens for which protective immunity could not otherwise be generated.

Suitable carrier proteins comprise conventionally-used carriers such as the highly immunogenic tetanus toxoid protein, *Plasmodium falciparum circumsporozite*, hepatitis B surface antigen, hepatitis B nuclear core protein, *H. influenzae* matrix protein, *H. influenzae* haemagglutinin diptheria toxoid, non-toxic diptheria toxin mutant CRM 197, group B *N. meningitidis* outer membrane protein complex (OMPC), the pneumococcal toxin pneumolysin, and heat shock proteins from *Mycobacterium bovis*. Other suitable carrier proteins will be known to those of skill in the art. Improved carrier proteins have recently been developed containing CD4+ $T_h$ cell epitopes that do not contain T cell suppressor functions; these carriers will also be suitable for use in conjunction with the compounds of the present invention.

In addition to carrier proteins, the compounds of the present invention may comprise other peptides or protein fragments, such as epitopes from immunomodulating cytokines such as interleukin-2 (IL-2) or granulocyte-macrophage colony stimulating factor (GM-CSF). Promiscuous peptides (Panina-Bordignon et al. 1989), the so-called "universal" peptides (Kumar et al., 1992), cluster peptides (Ahlers et al., 1993) or peptides containing both T cell and B cell epitopes (Lett et al., 1994) may also be used to recruit various effector systems of the immune system, as required.

The peptide, oligopeptide or polypeptide compounds of the present invention may be generated by any suitable means, as will be apparent to those of skill in the art. In the case of peptides, combinatorial peptide libraries will be most suitable; peptide molecules displaying the desired binding characteristics can be isolated through selection regimes that select for molecules that bind to antibodies that are specific for GBS capsular polysaccharide, preferably type III capsular polysaccharide (for example the anti-type III CHO mAb P9D8).

One method of generation of peptide libraries utilises degenerate oligonucleotide libraries. This method allows the subsequent analysis of the encoding nucleic acid and thus gives direct sequence information for the mimotope (see for example, Cull et al. 1992; Matteakis et al., 1994).

Phage display technology also provides a vehicle that allows for the selection of displayed peptides, oligopeptides or polypeptides and simultaneously provides a link between phenotype and genotype so that the encoding nucleic acid can be identified and analysed (for a review see Clackson and Wells (1994) *Trends Biotechnol* 12: 173–184). Filamentous phage particles act as genetic display packages with proteins on the outside and the nucleic acids which encode them on the inside. The practical limit on library sise allowed by this technology is of the order of $10^7$ to $10^{11}$ variants, so allowing the generation of a huge number of different compounds. This technology also allows iterative rounds of selection to be performed, so honing the affinity of the molecules isolated.

The preferred method of generation of peptide, oligopeptide or polypeptide compounds according to the present invention is through selection of candidate compounds in a phage display library.

Selection of a nucleic acid or gene from a phage display library will in most cases require the screening of a large number of variant nucleic acids or genes. Libraries of nucleic acids or genes for use with phage display technology may be generated in a variety of ways. For example, pools of naturally-occurring genes may be cloned from genomic DNA or cDNA (see Sambrook et al., 1989). Phage-antibody libraries, made by PCR amplification repertoires of antibody genes from immunised or non-immunised donors have proved very effective sources of functional antibody fragments (Winter et al., (1994) *Annu Rev Immunol,* 12, 433–55; Hoogenboom, (1997) *Trends Biotechnol.,* 15, 62–70).

Preferably, the compounds of the present invention are produced in phage display libraries containing nucleic acid pools derived from the mRNA of splenic lymphocytes of animals that have been immunised with anti-GBS antibody. Preferably the antibody used for immunisation of the animal is directed against the type III CHO of GBS. Most preferably, the antibody used is the P9D8 antibody.

Libraries of genes can also be made by encoding all or part of genes or pools of genes or by using randomised or doped synthetic oligonucleotides. Libraries can also be made by randomly introducing mutations into a gene or into a pool of genes by a variety of techniques in vivo, including using so-called 'mutator strains' of bacteria such as *E. coli* mutD5 (Liao et al., 1986). The antibody hypermutation system of B-lymphocytes may also be used (Yelamos et al., 1995).

Random mutations can also be introduced both in vivo and in vitro by chemical mutagens, and ionizing or UV irradiation (see Friedberg et al., 1995), or by incorporation of mutagenic base analogues (Zaccolo et al., 1996). Mutations can also be introduced into genes in vitro during polymerisation, for example by using error-prone polymerases (Leung et al., 1989). Further diversification can be introduced by using homologous recombination either in vivo (see Kowalczykowski et al., 1994) or in vitro (Stemmer, 1994).

Once the peptide, oligopeptide, or polypeptide compound of the invention has been isolated, the compound may be produced in larger amounts by any suitable means, as will be apparent to those of skill in the art. Two preferred methods of construction are direct synthesis and by production of recombinant protein. In the case of short peptides whose sequence is known, the preferable method of production may be by direct synthesis. However, in most cases, the preferable method will be by recombinant means, by expression from an encoding nucleic acid molecule. Recombinant expression has the advantage that the production of the compound is inexpensive, safe, facile and does not involve the use of toxic compounds that may require subsequent removal.

When expressed in recombinant form, the compounds of the present invention will be generated by expression from an encoding nucleic acid in a host cell. A variety of different expression systems may be used, for example those used with mammalian cells, baculoviruses, bacteria, and yeast. Preferably, bacterial hosts are used for the production of recombinant protein, due to the ease with which bacteria may be manipulated and grown. The bacterial host of choice is *Escherichia coli.*

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual,* 2nd ed].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) Proc. Natl. Acad. Sci. 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) Science 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells. Usually, transcription termination and polyadenylation sequences recognised by mammalian cells are regulatory regions located 3' to the translation stop codon and thus, together with the promoter elements, flank the coding sequence. The 3' terminus of the mature mRNA is formed by site-specific post-transcriptional cleavage and polya-denylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem* 55:1119; Krainer and Maniatis (1988) "RNA splicing." In *Transcription and splicing* (ed. B. D. Hames and D. M. Glover)].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems., thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946 and pHEBO [Shimizu et al. (1986) *Mol. Cell. Biol* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Mammalian cell lines available as hosts for expression are known in the art and include many immortalised cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

The polynucleotide encoding the protein can also be inserted into a suitable insect expression vector, and is operably linked to the control elements within that vector. Vector construction employs techniques that are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, INVITROGEN, San Diego Calif. ("MAXBAC" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.,* 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognised by insect cells, and the signals required for secretion and nuclear accumulation also appear to be conserved between the invertebrate cells and vertebrate cells, leaders of non-insect origin, such as those derived from genes encoding human γ-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of non-fused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols of Microbiology" Vol. 2 (Ausubel et al. eds) at 16.8 (Supp. 10, 1990): Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (PCT Pub. No. WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include the promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EPO Publ. Nos. 036 776 and 121 775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21] Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EPO Publ. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; EPO Publ. No. 244 042].

Usually, transcription termination sequences recognised by bacteria ate regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in E. coli as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) Annu. Rev. Microbiol. 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: Bacillus subtilis [Palva et al. (1982) Proc. Natl. Acad. Sci. USA 79:5582; EPO Publ. Nos. 036 259 and 063 953; PCT Publ. No. WO 84/04541], Escherichia coli [Shimatake et al. (1981) Nature 292:128; Amann et al. (1985) Gene 40:183; Studier et al. (1986) J. Mol. Biol. 189:113; EPO Publ. Nos. 036 776, 136 829 and 136 907], Streptococcus cremoris [Powell et al. (1988) Appl. Environ. Microbiol. 54:655]; Streptococcus lividans [Powell et al. (1988) Appl. Environ Microbiol. 54:655], Streptomyces lividans [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) FEMS Microbiol. Lett. 60:273; Palva et al. (1982) Proc. Natl. Acad. Sci. USA 79:5582; EPO Publ. Nos. 036 259 and 063 953; PCT Publ. No. WO 84/04541, Bacillus], [Miller et al. (1988) Proc. Natl. Acad. Sci. 85:856; Wang et al. (1990) J. Bacteriol. 172:949, Campylobacter], [Cohen et al. (1973) Proc. Natl. Acad. Sci. 69:2110; Dower et al. (1988) Nucleic Acids Res. 16:6127; Kushner (1978) "An improved method for transformation of Escherichia coli with ColE1-derived plasmids. In Genetic Engineering: Proceedings of the International Symposium on Genetic Engineering (eds. H. W. Boyer and S. Nicosia); Mandel et al. (1970) J. Mol. Biol. 53:159; Taketo (1988) Biochim. Biophys. Acta 949:318; Escherichia], [Chassy et al. (1987) FEMS Microbiol. Lett. 44:173 Lactobacillus]; [Fiedler et al. (1988) Anal. Biochem 170:38, Pseudomonas]; [Augustin et al. (1990) FEMS Microbiol. Lett. 66:203, Staphylococcus], [Barany et al. (1980) J. Bacteriol. 144:698; Harlander (1987) "Transformation of Streptococcus lactis by electroporation, in: Streptococcal Genetics (ed. J. Ferretti and R. Curtiss III); Perry et al. (1981) Infect. Immun 32:1295; Powell et al. (1988) Appl. Environ. Microbiol. 54:655; Somkuti et al. (1987) Proc. 4th Evr. Cong. Biotechnology 1:412, Streptococcus].

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences [Myanohara et al. (1983) Proc. Natl. Acad. Sci. USA 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588, 684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognised by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognised termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17–24], pCl/1 [Brake et al. (1984) *Proc. Natl. Acad. Sci USA* 81:4642–4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750].

The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRR.1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. (1985) *J. Basic Microbiol.* 25:141; Candida]; [Gleeson et al. (1986) *J. Gen. Microbiol.* 132:3459; Roggenkamp et al. (1986) *Mol. Gen. Genet.* 202:302; Hansenula]; [Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; Pichia]; [Hinnen et al. (1978) *Proc. Natl. Acad. Sci. USA* 75;1929; Ito et al. (1983) *J. Bacteriol.* 153:163 Saccharomyces]; [Beach and Nurse (1981) *Nature* 300:706; Schizosaccharomyces]; [Davidow et al. (1985) *Curr. Genet.* 10:39; Gaillardin et al. (1985) *Curr. Genet.* 10:49; Yarrowia].

According to a further aspect of the present invention there is provided a method of production of a compound according to the first aspect of the present invention, comprising the steps of:

a) immunising a mammal with an antibody against a capsular polysaccharide of group *B Streptococcus*;

b) removing spleen cells from the immunised mammal and selecting for cells that bind to the antibody;

c) separating mRNA species from selected spleen cells and producing a phage library expressing proteins encoded by the mRNA species;

d) selecting for recombinant phage expressing compounds of interest.

In order to immunise the mammal, an antibody against capsular polysaccharide of group *B Streptococcus* (preferably type III CHO) is introduced, preferably parenterally, in an amount sufficient to elicit an immune response. The choice of mammal for immunisation will depend largely upon the mammal for which the protective compound is intended. In most cases, this will be the human. Immunisation will most preferably utilise the antibody P9D8 (Teti et al., 1992). Splenic lymphocytes are then removed from the immunised patient and cells are selected by antigen panning using the antibody that was used for the initial immunisation as the coating antigen. mRNA from the selected lymphocytes is then used as a template for reverse transcriptase and the resulting cDNA can then be used to construct a recombinant phage library that expresses recombinant peptides, oligopeptides or polypeptides as fusion proteins with gIIIp. Phage expressing suitable candidate compounds on their surface may again be selected by affinity purification using the antibody initially used for immunisation as the coating antigen. These phage can then be analysed using methods that will be readily apparent to those of skill in the art.

According to a further aspect of the present invention, there is provided a composition comprising a peptide, oligopeptide, or polypeptide compound that is capable of eliciting a protective immune response against the capsular polysaccharide of group *B Streptococcus,* preferably the type III CHO of GBS, in conjunction with a pharmaceutically acceptable excipient. Such a composition may be used to provide protection against disease caused by pathogenic GBS bacteria and accordingly, may be used as a vaccine. Vaccines according to the invention may either be prophylactic (ie. to prevent infection) or therapeutic (ie. to treat disease after infection).

By pharmaceutically-acceptable excipient is meant any compound that does not itself induce the production of antibodies harmful to the individual receiving the composition. The excipient should be suitable for oral, subcutaneous, intramuscular, topical or intravenous administration. Suitable compounds are typically large, slowly metabolised macromolecules such as proteins, polysaccharides, polylactic acids, polyglycolic acids, polymeric amino acids, amino acid copolymers, lipid aggregates (such as oil droplets or liposomes) and inactive virus particles. Such compounds are well known to those of skill in the art. Additionally, these compounds may function as immunostimulating agents ("adjuvants"). Furthermore, the antigen may be conjugated to a bacterial toxoid.

Preferred adjuvants to enhance effectiveness of the composition include, but are not limited to: (1) aluminium salts (alum), such as aluminium hydroxide, aluminium phosphate, aluminium sulphate, etc; (2) oil-in-water emulsion formulations (with or without other specific immunostimulating agents such as muramyl peptides or bacterial 5 cell wall components), such as for example (a) MF59™ (WO 90/14837), containing 5% Squalene, 0.5% TWEEN 80, and 0.5% SPAN 85 (optionally containing various amounts of MTP-PE, although not required) formulated into submicron particles using a microfluidizer (b) SAF, containing 10% Squalane, 0.4% TWEEN 80, 5% pluronic-blocked polymer L121, and thr-MDP either microfluidised into a submicron emulsion or vortexed to generate a larger particle size emulsion, and (c) RIBI adjuvant system (RAS), containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL+CWS (DETOX); (3) saponin adjuvants, such as STIMULON may be used or particles generated therefrom such as ISCOMs (immunostimulatingg complexes); (4) Freud's complete and incomplete adjuvants (CFA & IFA); (5) cytokines, such as interleukins (eg. IL-1, IL-2, IL-4, IL-5, IL-6, IL-7, IL-12, etc.), interferons (eg. IFNγ), macrophage colony stimulating factor (M-CSF), tumor necrosis factor (TNF), etc; and (6) other substances that act as immunostimulating agents to enhance the efficacy of the composition. Alum and MF59™ are preferred.

As mentioned above, muramyl peptides include, but are not limited to, N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (eg. the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvanticity effect, as discussed above.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally eg. by injection, either subcutaneously or intramuscularly. They may also be administered to mucosal surfaces (eg. oral or intranasal), or in the form of pulmonary formulations, suppositories, or transdermal applications. Dosage treatment may be a single dose schedule or a multiple dose schedule. The vaccine may be administered in conjunction with other immunoregulatory agents.

Peptide, oligopeptide, or polypeptide compounds according to the invention can also be used in immunoassays to detect antibody levels (or, conversely, antibodies directed against the compounds of the present invention can be used to detect antigen levels). Immunoassays based on well-defined, recombinant antigens can be developed to replace invasive diagnostics methods. Antibodies to the compounds of the present invention within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labelled antibody or polypeptide; the labels may be, for example, fluorescent, chemiluminescent, radioactive, or dye molecules. Assays which amplify the signals from the probe are also known; examples of which are assays which utilise biotin and avidin, and enzyme-labelled and mediated immunoassays, such as ELISA assays.

The invention also provides kits suitable for immunodiagnosis. These contain the appropriate labelled reagents and are constructed by packaging the appropriate materials, including the compositions of the invention, in suitable containers, along with the remaining reagents and materials (eg. suitable buffers, salt solutions, etc.) required for the conduct of the assay, as well as suitable set of assay instructions.

As an alternative to protein-based vaccines, DNA vaccination may be employed [eg. Robinson & Torres (1997) *Seminars in Immunology* 9:271–283; Donnelly et al. (1997) *Annu Rev Immunol* 15:617–648]. Accordingly, rather than comprise a peptide, oligopeptide, or polypeptide compound, the vaccines of the invention might comprise nucleic acid encoding these compounds.

According to a still further aspect of the present invention there is provided a method of prevention or treatment of a disease caused by GBS comprising introducing into a mammal, preferably a human, a compound or a composition that is capable of eliciting a protective immune response against the capsular polysaccharide of GBS in an effective amount.

According to a still further aspect of the present invention, there is provided a method of vaccinating a mammal, preferably a human, against a disease caused by GBS, comprising administering to the mammal a composition of a peptide, oligopeptide, or polypeptide compound according to the first aspect of the invention, optionally with a pharmaceutically-acceptable carrier such as an adjuvant.

According to a further embodiment of the present invention, there are also provided nucleic acid molecules encoding peptides, oligopeptides and polypeptides according to the first aspect of the invention. As will be apparent to the skilled artisan, the sequence of these nucleic acid molecules defines the amino acid sequence of the peptide, oligopeptide or polypeptide that possesses the desired activity through the specificity of the genetic code.

Additionally, in order to precisely tailor the exact properties of the encoded compounds, the skilled artisan will appreciate that changes may be made at the nucleotide level from the peptide, oligopeptide or polypeptide sequence originally isolated, by addition, substitution, deletion or insertion of one or more nucleotides. Site-directed mutagenesis (SDM) is the method of preference used to generate mutated, improved compounds according to the present invention. There are many techniques of SDM now known to the skilled artisan, including oligonucleotide-directed mutagenesis using PCR as set out, for example by Sambrook et al., (1989) or using commercially available kits.

Most compounds produced by such techniques of mutagenesis will be less efficacious than those originally selected. However, in a minority of cases, the introduced mutations will produce molecules with improved function, such as closer structural similarity to the type III CHO epitope of GBS, or greater immunogenicity in a certain organism.

The nucleic acid molecules according to this aspect of the present invention may comprise DNA, RNA or cDNA and may additionally comprise nucleotide analogues in the coding sequence. Preferably, the nucleic acid molecules comprise DNA.

A further aspect of the present invention provides a host cell containing a nucleic acid encoding a compound according to the first aspect of the invention. A still further aspect provides a method comprising introducing the encoding nucleic acid into a host cell or organism. Introduction of nucleic acid may employ any available technique, as discussed above.

In one embodiment, the nucleic acid is integrated into the genome of the host cell. Integration may be promoted by the inclusion of sequences that promote recombination with the genome, in accordance with standard techniques (see Sambrook et al., 1989).

Transgenic animals transformed so as to express or overexpress in the germ line one or more peptide, oligopeptide or polypeptide compounds according to the first aspect of the present invention form a still further aspect of the invention, along with methods for their production.

Various aspects and embodiments of the present invention will now be described in more detail by way of example, with particular reference to scFv compounds isolated from a phage library. It will be appreciated that modification of detail may be made without departing from the scope of the invention. All publications, patents, and patent applications cited herein are incorporated in full by reference.

DETAILED DESCRIPTION OF THE INVENTION

Summary of Standard Procedures and Techniques

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual*, Second Edition(1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilised Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I–IV* (D. M. Weir and C. C. Blackwell eds 1986).

EXAMPLES

Statistical Analysis.

Differences between antibody concentrations in mouse sera were analysed for statistical significance using one way analysis of variance and the Student-Keuls-Newman test. Differences in lethality were analysed with Fisher's exact test.

Bacterial Strains and Reagents.

Strain H738 (type III), was kindly provided by Dr. Bascom Anthony, National Institutes of Health, Bethesda, Md. Strain COH1 (also GBS type III) and the unencapsulated isogenic mutant COH1–13 were a gift of Dr. Craig Rubens, University of Washington, Seattle (Rubens et al., 1987). Type III and group-specific CHOs were purified by ion-exchange chromatography and gel filtration from the culture supernatant of strain H738, as described previously (Mancuso et al., 1994; von Hunolstein et al., 1997). The type III CHO contained 24% sialic acid by weight (Aminoff, 1961). This preparation was considered of sufficient purity because it contained, on a weight basis, <0.5% proteins (BIORAD protein assay, BioRad Laboratories, Milan, Italy) nucleic acids (absorbance at 250 nm) or rhamnose (Dische and Shettles, 1948), a major constituent of the group antigen.

The properties and purification of murine mAb P9D8 have been described elsewhere (Teti et al., 1992). This mAb binds to a sialic acid-dependent epitope of the type III CHO, promotes opsonophagocytic killing of GBS and has significant protective activities against GBS-induced lethality when passively administered to neonatal rats or mice.

Rabbit anti-type III GBS serum (Statens Serum Institute, Copenhagen, Denmark) was absorbed with heat-killed (80° C. for 45 min) unencapsulated GBS (strain COH1–13) to remove non-type specific anti-GBS antibodies. After absorption, this preparation reacted with type III GBS, but not with unencapsulated strains or strains belonging to other serotypes.

Production of Phage Libraries.

Phage libraries were produced using the following protocol. Male BALB/c mice (8 weeks old) were subcutaneously (s.c.) injected on days 0 and 15 with 50 μg of mAb P9D8 in 0.2 ml of complete Freund's adjuvant (Difco, distributed by Diagnostic International Distributors, Milan, Italy) and on days 21 and 28 with the same dose of antigen in 0.2 ml of incomplete Freund's adjuvant (Difco). A final booster injection (50 μg of antigen in saline) was given intraperitoneally on day 35, and three days later the mice were sacrificed and their spleens removed.

Spleen cells were resuspended in tissue culture medium and dispensed into 75 $cm^2$ tissue culture flasks previously coated with mAb P9D8 (25 μg/ml) in carbonate buffer (pH 9.6) and blocked with 2% non-fat dry milk (Sigma, Milan, Italy).

After overnight incubation at 37° C. in 5% $CO_2$. non-adherent spleen cells were removed and mRNA was extracted from adherent cells directly in the panning flask using guanidium isothiocyanate. After purification by affinity chromatography on oligo(dT)- cellulose ( QUICKPREP mRNA purification kit, Pharmacia, Biotech, Milan, Italy), reverse- transcription of the purified mRNA was performed with a murine reverse transcriptase by priming with random hexadeoxyribonucleotides, as described by Magliani et al. (1997).

To clone and express antibody fragments, a commercial system ( RECOMBINANT PHAGE ANTIBODY SYSTEM, Pharmacia) was used. The heavy and light chain antibody genes were amplified in two separate PCR reactions, by using two sets of specific primers, to generate 340 and 325 base pair fragments, respectively. The heavy and light chain DNA products were assembled into a single gene using a DNA fragment encoding a $(Gly_4Ser)_3$ linker, acting as a bridge between the carboxy-terminus of the $V_H$ chain and the amino-terminus of the $V_L$ chain. The gene was then reamplified to introduce two restriction sites (Sfi I/Not I) for cloning into a specific phagemid vector (pCANTAB 5E).

The ligated vector, containing the scFv genes linked to a sequence encoding for a C-terminal 13 amino acid peptide tag (E-tag) and followed by an amber translation stop codon, was introduced into a competent supE *E. coli* strain (TG1) which was then infected with the M13KO7 helper phage to yield recombinant phages displaying recombinant scFv antibodies on their tips.

Phage Selection.

Phage selection was performed using the following protocol. Recombinant phages were dispensed to a 25 cm² tissue culture flask that had been previously coated with 5 ml of mAb P9D8 (10 μg/ml) in carbonate buffer (pH 9.6). After an incubation of 2 hours at 37° C. and extensive washing, log-phase TG1 cells were added to the flask and incubated at 37° C. for 1 hour. The suspension was transferred into sterile tubes and, after the addition of ampicillin (100 μg/ml), glucose (2%) and M13KO7 helper phage, further incubated with shaking at 37° C. After production of the recombinant phage supernatant, a second round of panning was repeated and the cells plated onto ampicillin-containing agar plates. Isolated colonies were transferred to separate wells of 96-well microtiter plates (master plates) which were then used for the library rescue with M13KO7.

Recombinant phage supernatants, obtained form the master plates were screened in the wells of microtiter plates previously coated with mAB P9D8 (10 μg/ml). 200μl of each supernatant, previously diluted with an equal volume of blocking buffer, were added to each antigen-coated well and incubated at room temperature for 2 hours. After 5 washings with 0.05% TWEEN 20 in PBS, bound phages were detected using 200 μl of peroxidase-conjugated sheep anti-M13 phage antibodies (Magliani et al., 1997).

After two pannings of the library, six different phage clones produced strong reactions in ELISA tests using again wells coated with mAb P9D8. One of these clones, designated as C10, was selected for further characterisation. In addition, the irrelevant H6 scFv (Magliani et al., 1997), which is unable to bind mAb P9D8, was selected as a control to be used throughout this study.

Production of scFv Recombinant Antibodies.

The recombinant phages giving a positive ELISA signal were used to infect *E. coli* HB2151 to produce soluble scFv recombinant antibodies.

Antigen-positive recombinant phages were used to infect log-phase HB2151 cells, which were exposed to 1 mM EDTA to obtain periplasmic extracts. The scFv recombinant molecules were also obtained from concentrated supernatants of HB2151 cultures. Purification of scFv from either periplasmic extracts or supernatants was performed using an anti-E-tag N-hydroxysuccinimide activated SEPHAROSE columns (HITRAP ANTI-E-TAG, Pharmacia, as described by Magliani et at., (1997). During purification, scFv were detected by dot or western blot using anti-E-tag antibody.

After infection of *E. coli* HB2151 cells, C10 and the control H6 scFv were produced from either the periplasmic extracts or concentrated supernatants of the transformed strain. Since higher amounts were obtained from the supernatants (6 mg/l), these were used as a preferential source of scFv in subsequent studies. Western blot analysis of affinity purified C10 or H6 scFv showed that both consisted of single monomers with the approximate molecular weight of 29 kDa (not shown).

GBS Agglutination Inhibition Assay.

In preliminary studies, soluble C10 and H6 scFv were tested for their ability to inhibit GBS agglutination by anti-type III antibodies.

A bacterial agglutination assay was set up by mixing killed GBS with type III-specific antibodies in U bottom-wells of microtiter plates. In this assay, type III GBS, but not unencapsulated mutants, were agglutinated by either mAb P9D8 or absorbed rabbit serum. For agglutination inhibition assay, inhibitors (50 μl in PBS supplemented with 1% bovine serum albumin) were mixed with an equal volume of antibody-containing solutions in the wells of microtiter plates. Antibody solutions were adjusted to achieve final dilutions corresponding to two times the minimal concentration needed to induce agglutination in the absence of inhibitors. After incubating the inhibitors with type-specific antibody or absorbed rabbit serum for 30 minutes at 37° C., 50 μl of the killed-GBS suspension was added. This suspension was obtained after killing GBS strain H738 (type III) in 3% formalin (3 days at 4° C.), and resuspending the washed pellet in PBS- albumin to a concentration of $5 \times 10^8$ cells/ml. The plates were incubated for 4 hours at 37° C. and then overnight at room temperature. Results were assessed visually.

The specificity of the test for the type III CHO was confirmed by the ability of purified type-, but not group-specific antigen, to inhibit the agglutination of type III GBS by mAb P9D8 (Table 1). C10 scFv, at 15 μg/ml or higher concentrations, was capable of inhibiting the agglutination of GBS cells induced by mAb P9D8. Significantly, up to 240 μg/ml of the irrelevant H6 scFv did not affect agglutination (Table 1). The inhibitory activities of C10 scFv suggested that the fragment recognised an idiotypic determinant of mAb P9D8 that was either close or identical to the paratopic combining site.

To discriminate between these two possibilities, agglutination-inhibition experiments were performed using rabbit anti-type III antibodies, in place of mAb P9D8, to induce agglutination. The rationale behind these studies is that idiotypes unrelated to antigen binding are rarely present in antibodies raised in different species (Westerink et al., 1990).

TABLE 1

Ability of anti-idiotypic scFv to inhibit GBS agglutination by type III-specific antibodies

| Anti-type III antibody | Inhibitor | Agglutination |
|---|---|---|
| None | None | − |
| mAb P9D8 ascites[a] | None | + |
| mAb P9D8 ascites | Type III CHO (5 μg/ml) | − |
| mAb P9D8 ascites | Group CHO (25 μg/ml) | + |
| mAb P9D8 ascites | C10 scFv (240 μg/ml) | − |
| mAb P9D8 ascites | C10 scFv (120 μg/ml) | − |
| mAb P9D8 ascites | C10 scFv (60 μg/ml) | − |
| mAb P9D8 ascites | C10 scFv (30 μg/ml) | − |
| mAb P9D8 ascites | C10 scFv (15 μg/ml) | − |
| mAb P9D8 ascites | C10 scFv (7.5 μg/ml) | + |
| mAb P9D8 ascites | H6 scFv (240 μg/ml) | + |
| Absorbed rabbit serum[b] | None | + |
| Absorbed rabbit serum | Type III CHO (5 μg/ml) | − |
| Absorbed rabbit serum | Group CHO (25 μg/ml) | + |
| Absorbed rabbit serum | C10 scFv (240 μg/ml) | − |
| Absorbed rabbit serum | C10 scFv (120 μg/ml) | − |
| Absorbed rabbit serum | C10 scFv (60 μg/ml) | − |

TABLE 1-continued

Ability of anti-idiotypic scFv to inhibit GBS agglutination by type III-specific antibodies

| Anti-type III antibody | Inhibitor | Agglutination |
| --- | --- | --- |
| Absorbed rabbit serum | C10 scFv (30 µg/ml) | + |
| Absorbed rabbit serum | H6 scFv (240 µg/ml) | + |

[a]Used at a final dilution of 1:125,000
[b]Used at a final dilution of 1:500

Table 1 shows that the C10 scFv was capable of inhibiting agglutination induced by rabbit antibodies. This strongly suggested that C10 scFv was specific for the antigen-binding site of anti-type III CHO antibodies, and that could, therefore, mimic the conformation of the nominal type III antigen.

Immunisation with scFv.

In further experiments, mice were immunised with 50 µg of soluble C10 or H6 scFv in order to determine the nature of the immune response generated against these molecules.

Male BALB/c mice (6 weeks old) were immunised with either purified scFv or polyethylene glycol-NaCl precipitated phage-displayed scFv (Magliani et al., 1997). A first subcutaneous injection of 50 µg of antigen in 0.2 ml of complete Freund's adjuvant was followed, after 2 weeks, by a second subcutaneous administration of the same dose in 0.2 ml of incomplete Freund's adjuvant. Three additional injections of 50 µg of immunogen in 0.2 ml of saline were given intraperitoneally at 21, 28 and 35 days after the initial immunisation.

Sera were obtained from the retroorbital plexus at the indicated times after immunisation and analysed for antibodies directed against the type III antigen using an enzyme-linked immunosorbent assay, in which microtiter plates were coated with 1 µg/well of tyrosylated type III CHO (Teti et al., 1992). Bound antibodies were detected with biotinylated polyvalent anti-mouse IgG (Vector Laboratories, distributed by Labtek Milan, Italy) or with µ- or γ chain-specific alkaline phosphatase-horse anti-mouse Ig (Sigma, Milan, Italy), as described by Teti et al., (1992a). A positive control consisting of pooled sera from mice immunised with killed type III GBS was included in each determination. Results were expressed in arbitrary units equal to the ratio between absorbance of test serum and absorbance of the positive control serum multiplied by 1,000.

Figure 1:
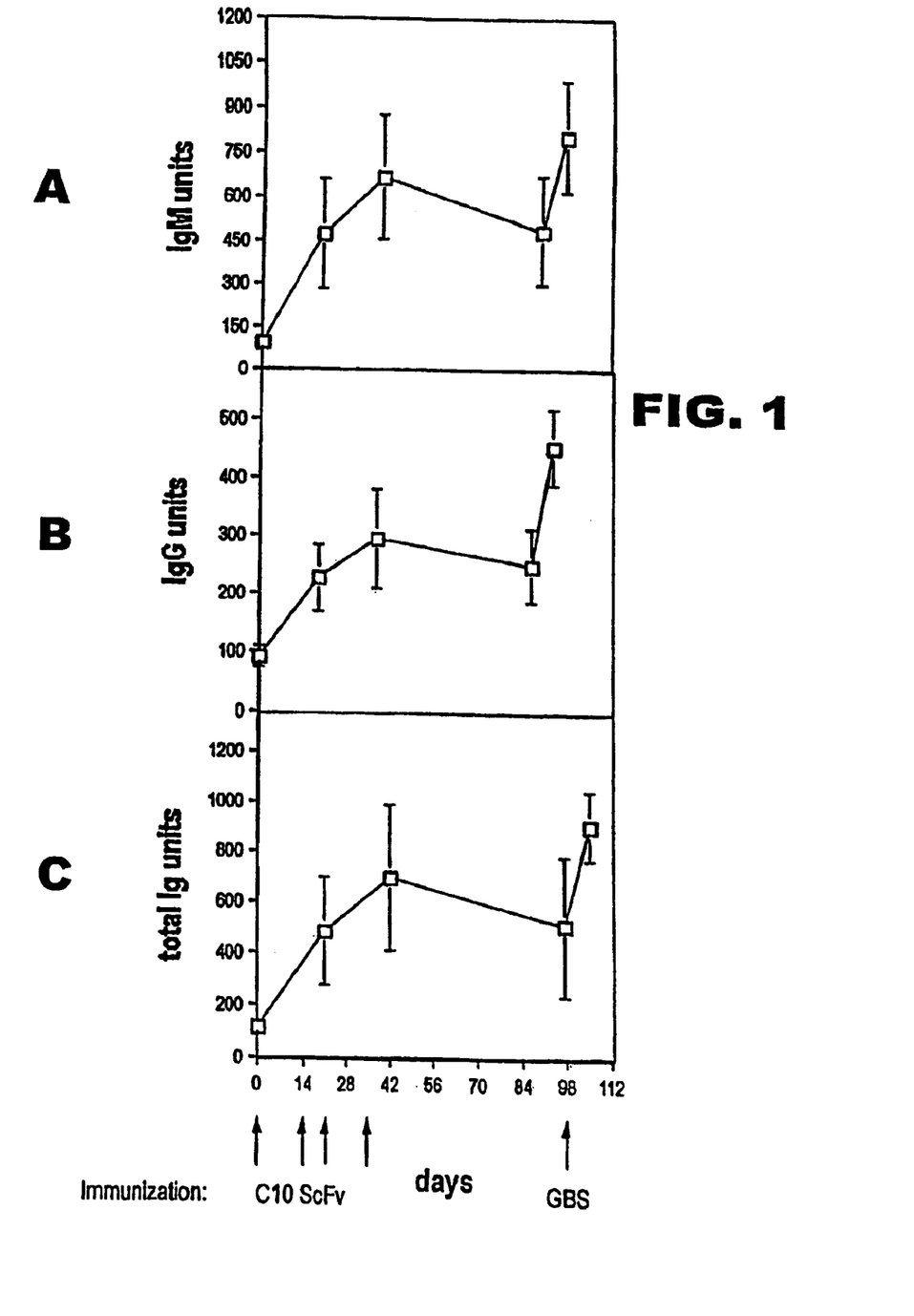
FIG. 1 shows anti-type III antibody levels in sera collected at various times after immunisation of mice with C10 scFv. Mice were immunised with purified C10 scFv or heat-killed GBS at the indicated times (arrows). Points and bars represent means±standard deviations of 5 determinations, each conducted on a different serum sample.
Figure 2:
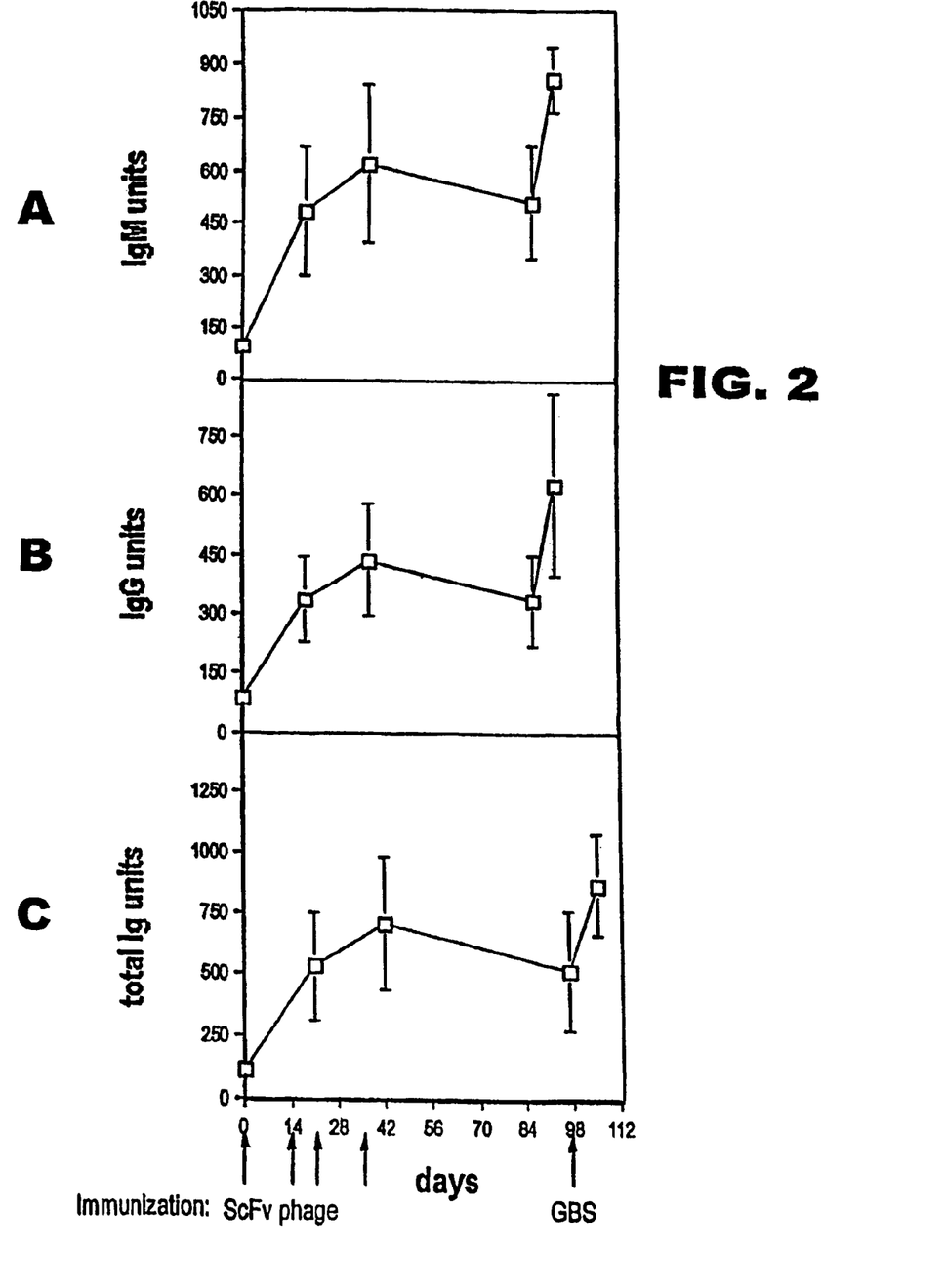
FIG. 2 shows anti-type III antibody levels in sera collected at various times after immunisation with phage-displayed C10 scFv. Mice were immunised with phages expressing the C10 scFv or heat-killed GBS at the indicated times (arrows). Points and bars represent means±standard deviations of 5 determinations, each conducted on a different serum sample.

FIGS. 1A, 1B, and 1C show ELISA results of serum samples (collected at the indicated times) tested for antibody levels by ELISA using the type III CHO as the coating antigen. Sera from mice vaccinated with C10 scFv showed significant (p<0.05) elevations in anti-type III IgM and IgG, as compared with preimmune values (FIGS. 1A, 1B, and 1C). In contrast, sera from mice immunised with the control H6 scFv did not show any significant anti-type III CHO response (not shown). C10 scFv-induced anti-type III CHO antibody elevations were boosted by repeated vaccinations and slowly declined after the last immunisation with scFv at day 35 (FIGS. 1A, 1B, and 1C).

In order to determine if these immunisations primed the mice for responding to the nominal antigen, C10 scFv-immunised animals were boosted with killed type III GBS at day 97. FIGS. 1A, 1B, and 1C show that killed bacteria produced a sharp rise in anti-type III CHO antibodies as evidenced by higher titers of IgM, IgG and total antibodies at day 104, relative to day 97 values. These data indicated that C10 scFv could prime the mice for increased responses upon exposure to the pathogen.

Further studies were conducted to determine whether phages displaying the C10 scFv on their surface could also induce anti-type III CHO responses. Anti-type III CHO antibody responses in mice immunised with phage-displayed C10 fragments (FIGS. 2A, 2B, and 2C) were quite similar to those observed with purified C10 scFv using the same immunisation schedule and doses (i.e. 50 μg of phages per mouse). Again, control phage-displayed H6 fragments were ineffective (not shown). These data suggest that presentation of the recombinant antiidiotypic fragments on the phage surface can be quite effective in inducing antibody responses, especially when taking into account that only 3–5 scFv molecules are expressed on the surface of each phage (Kortt et al., 1994).

Neonatal Model of GBS Disease.

To study the protective effects of passively administered sera, a neonatal mouse model of GBS infection was used (Mancuso et al., 1994; Cusumano et al., 1996; Mancuso et al., 1997) so that the ability of C10 scFv to passively protect pups against lethal infection with highly virulent GBS could be evaluated. The same model was also employed to assess the efficacy of active maternal immunisation in protecting neonates from infection.

To assess the protective activity of sera, neonatal (24 h old) Balb/c mice were randomly assigned to control or experimental groups, marked and kept with the mother. Pups were inoculated subcutaneously with 25 μl of the indicated dilutions of normal or immune sera. Six hours later, the animals were challenged subcutaneously with the COH1 strain (100 CFU in 25 μl in PBS; a 90% lethal dose of GBS). Mortality was assessed every 12 hours for 5 days. Deaths rarely occurred after this time.

Table 2 shows that sera from either soluble or phage-displayed C10 scFv-immunised mice were capable of conferring significant passive immunoprotection against GBS challenge, as compared with preimmune sera. The protective titers of sera from C10 scFv-immunised mice ranged between 1:10 and 1:40 (Table 2). In contrast, sera from animals immunised with the irrelevant H6 scFv were non-protective (Table 2).

To determine whether maternal immunisation with anti-idiotypic fragments was effective in protecting neonatal mice against infection, 4 weeks-old female mice were immunised 3 times with 50 μg of soluble or phage-displayed scFv, mated and boosted again at 35 days after the initial immunisation. A first s.c. injection of 50 μg of antigen in 0.2 ml of complete Freund's adjuvant was followed after 2 weeks by a second s.c. administration of the same dose in 0.2 ml of incomplete Freund's adjuvant. One additional injection of 50 μg of immunogen in 0.2 ml of saline, was given s.c. at 21 days after the initial immunisation. Females were then mated at 31 days and boosted at 35 days with 50 μg of antigen in saline administered s.c.

Neonatal pups were then infected with a 90% lethal dose of GBS. Table 3 shows that neonates born to mothers immunised with soluble or phage-displayed C10 scFv were significantly protected against GBS-induced lethality, relative to those born to mothers immunised with the irrelevant H6 scFv.

TABLE 2

Effects on lethality of sera from scFv-immunised mice in a neonatal model of GBS disease

| Treatment | \multicolumn{5}{c}{Serum dilutions} | | | | |
|---|---|---|---|---|---|
| | 1:5 | 1:10 | 1:20 | 1:40 | 1:80 |
| Preimmune serum | 10/12[a] | 12/13 | 23/26 | 20/22 | |
| Anti-H6 scFv serum | 4/5 | 6/8 | 9/10 | | |
| Anti-C10 scFv serum no. 1 | 0/4[b] | 0/5[b] | 1/10[b] | 2/10[b] | 4/7 |
| Anti-C10 scFv serum no. 2 | | 0/9[b] | 1/13[b] | 7/8 | |
| Anti-C10 scFv serum no. 3 | | 0/9[b] | 6/8 | 7/7 | |
| Anti-C10 scFv serum no. 4 | | | 1/10[b] | 3/10[b] | 4/4 |
| Anti-C10 scFv serum no. 5 | | | 2/12[b] | 7/10 | |
| Anti-C10 phage-scFv no. 1 | 0/10[b] | 2/8[b] | 10/10 | | |
| Anti-C10 phage-scFv no. 2 | | | 0/5[b] | 0/4[b] | 4/5 |
| Anti-C10 phage-scFv no. 3 | | | 2/10[b] | 1/11[b] | 8/10 |

[a]Dead/total no. at 5 days after challenge. Shown are cumulative results from 5 experiments. Neonatal mice were injected s.c. with 20 µl of serum dilutions and infected with 100 CFU of GBS.
[b]Significantly different from normal serum by Fisher's exact test

TABLE 3

GBS-induced lethality in neonatal mice born to mothers immunised with anti-idiotypic scFv.

| Immunizing antigen | Neonatal lethality dead/total (%) |
|---|---|
| H6 scFv (control) | 19/21 (90) |
| C10 scFv | 8/35 (23)[a] |
| phage-H6 scFv (control) | 19/22 (86) |
| phage-C10 scFv | 5/31 (16)[a] |

[a]Significantly different from control by Fisher's exact test

REFERENCES

Ahlers J. D., (1993) *J. Immunol.* 150: 5647–5665.

Ala'Aldeen, D. A. A., & Hormaeche, C. E. (ed.). Molecular and clinical aspects of bacterial vaccine development. John Wiley & Sons, Chichester, U. K. (1995).

Aminoff, D. Methods for the quantitative estimation of N-acetylneuramic acid and their applications to hydrolisates of sialomucoids. Biochem. J. 81,384–390 (1961).

Baker, C. J., Edwards, M. S., & Kasper, D. L. Role of antibody to native type III polysaccharide of group *B streptococcus* in infant infection. Pediatrics 68,544–549 (1981).

Baker, C. J., Rench, M. A., Hickman, M. E., Paoletti, L. C., & Kasper, D. L. Safety and immunogenicity of group B streptococcal (GBS) polysaccharide (PS) types Ia and Ib-tetanus toxoid (Ia-TT; Ib-TT) conjugate vaccines in women (abstract). Pediatr. Res. 39,980A (1996).

Baker, C. J., & Edwards, M. S. Group B streptococcal infections. In: Remington J., Klein J. O., eds. Infectious diseases of the fetus and newborn infant. 4th ed. Philadelphia: W. B. Saunders, 980–1054 (1995).

Baker, C. J., & Kasper, D. L. Correlation of maternal antibody deficiency with susceptibility to neonatal group B streptococcal infection. N. Engl. J. Med. 294,753–756 (1976).

Clackson and Wells (1994) *Trends Biotechnol* 12: 173–184.

Cull et al. (1992) *P.N.A.S. USA* 89:1865–1869.

Cusumano, V. et al. Role of gamma interferon in a neonatal mouse model of group B streptococcal disease. Infect. Immun. 64,2941–2944 (1996).

Dische, Z., & Shettles, R. B. A specific color reaction of methylpentoses and a spectrophotometric micromethod for their determination. J. Biol. Chem. 17,595–599 (1948).

Friedberg et al., (1995) *DNA repair and mutagenesis*. ASM Press, Washington.

Hoogenboom, (1997) *Trends Biotechnol.*, 15, 62–70.

Kasper, D. L. et al. Immune response to type III streptococcal polysaccharide-tetanus toxoid conjugate vaccine. J. Clin. Invest. 98,2308–2314 (1996).

Kortt, A. A. et al. Recombinant antineuraminidase single chain Fv antibody: characterisation, formation of dimer and higher molecular mass multimers and the solution of the crystal structure of the scFv-neuraminidase complex. Eur. J. Immunol. 23, 206–211 (1994).

Kowalczykowski et al., (1994) *Microbiol Rev,* 58: 401–465.

Kumar A, Arora R, Kaur P, Chauhan V S, Sharma P (1992) "Universal" T helper cell determinants enhance immunogenicity of a *Plasmodium falciparum* merozoite surface antigen peptide. *J Immunol* 148: 1499–1505.

Larsonn, C., Stålhammar-Carlemalm, M., & Lindahl, G. Experimental vaccination against group *B streptococcus,* an encapsulated bacterium, with highly purified preparations of cell surface proteins rib and a. Infect. Immun. 64,3518–3523 (1996).

Lett, E. et al., (1994) *Infect Immun* 785–792.

Leung et al., (1989) *Technique*, 1: 11–15.

Liao et al., (1986) *P.N.A.S. USA*, 83: 576–580.

Madoff, L. C., Michel, J. L., Gong, E. W., Rodewald, A. K., & Kasper, D. L. Protection of neonatal mice from group B streptococcal infection by maternal immunisation with beta c protein. Infect. Immun. 60,4989–4994 (1992).

Magliani, W. et al. Therapeutic potential of antiidiotypic single chain antibodies with yeast killer toxin activity. Nature Biotechnol. 15,155–158 (1997).

Mancuso, G. et al. Beneficial effects of interleukin 6 in neonatal mouse models of group B streptococcal disease. Infect. Immun. 62,4997–5002 (1994).

Mancuso, G. et al. Role of interleukin 12 in experimental neonatal sepsis caused by group B streptococci. Infect. Immun. 65,3731–3735 (1997).

Mancuso, G., Tomasello, F., von Hunolstein, C., Orefici, G., & Teti, G. Induction of tumour necrosis factor alpha by the group- and type-specific polysaccharides from type III group B streptococci. Infect. Immun. 62:2748–2753 (1994).

Matteakis et al., (1994) *P.N.A.S. USA* 91: 9022–9026

McNamara, M., Ward, R. E., & Kohler, I. J. Monoclonal idiotype vaccine against *Streptococcus pneumonie* infection. Science 226,1325–1326 (1984).

Panina-Bordignon P, et al., (1989) *Eur J Immunol.* 19: 2237–2242.

Paoletti, L. C. et al. Neonatal mouse protection against infection with multiple group B streptococcal (GBS) serotypes by maternal immunisation with a tetravalent GBS polysaccharide-tetanus toxoid conjugate vaccine. Infect. Immun. 62,3236–3243 (1994).

Rubens, C. E., Wessels, M. R., Heggen, L. M., & Kasper, D. L. Transposon mutagenesis of group B streptococcal type III capsular polysaccharide: correlation of capsule expression with virulence. Proc. Natl. Acad. Sci. USA 84,7208–7212 (1987).

Stein, K. E., & Soderstrom, T. Neonatal administration of idiotype or anti-idiotype primes for protection against *E. coli* K13 infection in mice. J. Exp. Med. 160,1001–1041 (1984).

Stemmer, (1994) *Nature,* 370: 389–391.

Teti, G. et al. Specificity and protective activity of murine monoclonal antibodies directed against the capsular polysaccharide of type III group B streptococci. Hybridoma 11,13–22 (1992).

Teti, G., Tomasello, F., & Mancuso, G. Synthesis and immunological properties of an O-stearoyl polysaccharide from group B streptococci. J. Immunol. Res. 4,67–72 (1992).

von Hunolstein, C. et al. Soluble antigens from group B streptococci induce cytokine production in human blood cultures. Infect. Immun. 65,4017–4021 (1997).

Westerink, M. A., Campagnari, A. A., Wirth, M. A., & Apicella, M. A. Development and characterisation of an anti-idiotype antibody to the capsular polysaccharide of *Neisseria meningitidis* serogroup C. Infect. Immun. 56,1120–1127 (1988).

Westerink, M. A., Muller, E., & Apicella, M. A. Anti-idiotypic antibodies to bacterial capsular polysaccharides. in: *Idiotypic network and disease* (eds. Cerney, J. & Hiernaux, J.) p.107 to 119 (American Society for Microbiology, Washington, D.C., 1990).

Winter et al., (1994) *Annu Rev Immunol,* 12, 433–55.

Yelamos et al., (1995) *Nature,* 376: 225–229.

Zaccolo et al., (1996) *J Mol Biol* 255: 589–603.

What is claimed is:

1. An isolated nucleic acid molecule which encodes an scFv fragment that is capable of eliciting a type III capsular polysaccharide-specific protective immune response against group *B Streptococcus.*

2. The nucleic acid molecule of claim 1 wherein the nucleic acid molecule is DNA.

3. A cloning or expression vector comprising the nucleic acid molecule according to either of claim 1 or 2.

4. The vector according to claim 3 which is a viral vector.

5. A isolated host cell transformed or transfected with the nucleic acid molecule of either of claim 1 or 2.

6. A isolated host cell transformed or transfected with the vector of claim 3.

7. The nucleic acid molecule of claim 1, wherein the structure of the scFv fragment mimics an antigenic determinant of the type III capsular polysaccharide of group *B Streptococcus.*

8. The nucleic acid molecule of claim 7 wherein the nucleic acid molecule is DNA.

9. A cloning or expression vector comprising the nucleic acid molecule according to either of claim 7 or 8.

10. The vector according to claim 9 which is a viral vector.

11. A isolated host cell transformed or transfected with the nucleic acid molecule of either of claim 7 or 8.

12. A isolated host cell transformed or transfected with the vector of claim 9.

* * * * *